US012569292B2

(12) United States Patent
Crews et al.

(10) Patent No.: US 12,569,292 B2
(45) Date of Patent: Mar. 10, 2026

(54) SURGICAL INSTRUMENT WITH ELECTRICAL CONNECTION, AND RELATED DEVICES, SYSTEMS, AND METHODS

(71) Applicant: INTUITIVE SURGICAL OPERATIONS, INC., Sunnyvale, CA (US)

(72) Inventors: Samuel T. Crews, Palomar Park, CA (US); John Ryan Steger, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 470 days.

(21) Appl. No.: 18/148,136

(22) Filed: Dec. 29, 2022

(65) Prior Publication Data

US 2023/0210584 A1     Jul. 6, 2023

Related U.S. Application Data

(60) Continuation of application No. 16/918,026, filed on Jul. 1, 2020, now Pat. No. 11,564,734, which is a (Continued)

(51) Int. Cl.
*A61B 18/14*          (2006.01)
*A61B 17/29*          (2006.01)
(Continued)

(52) U.S. Cl.
CPC .......... *A61B 18/1447* (2013.01); *A61B 17/29* (2013.01); *A61B 18/1445* (2013.01);
(Continued)

(58) Field of Classification Search
CPC . A61B 18/1447; A61B 18/1445; A61B 34/35; A61B 34/30; A61B 17/29;
(Continued)

(56) References Cited

U.S. PATENT DOCUMENTS

| 5,395,369 A | 3/1995 | McBrayer et al. |
| 5,396,900 A | 3/1995 | Slater et al. |

(Continued)

FOREIGN PATENT DOCUMENTS

| CN | 201752400 U | 3/2011 |
| CN | 102264307 A | 11/2011 |

(Continued)

OTHER PUBLICATIONS

Office Action for Chinese Application No. CN202110773839.9, mailed Nov. 30, 2023, 18 pages.

(Continued)

*Primary Examiner* — Beverly M Flanagan
(74) *Attorney, Agent, or Firm* — Jones Burke, PLLC

(57)          ABSTRACT

An apparatus configured to deliver electrical energy to energize an end effector coupled via a clevis to a shaft of a medical instrument comprises an electrical transmission conduit configured to extend along the shaft from a proximal portion to a distal portion and configured to deliver electrical energy to energize the end effector, and a connector assembly configured to couple to the end effector. The connector assembly comprises an electrically conductive contact portion configured to electrically couple the electrical transmission conduit to the end effector, the electrically conductive contact portion defining a pivot surface about which the end effector is rotatable in a coupled state of the connector assembly to the end effector; and an electrically insulating (Continued)

member configured to electrically insulate the end effector from the clevis in a coupled state of the connector assembly to the end effector.

18 Claims, 12 Drawing Sheets

Related U.S. Application Data continuation of application No. 15/348,127, filed on Nov. 10, 2016, now Pat. No. 10,716,617, which is a division of application No. 14/209,043, filed on Mar. 13, 2014, now Pat. No. 9,498,242.

(60) Provisional application No. 61/803,046, filed on Mar. 18, 2013.

(51) Int. Cl.
| | | |
|---|---|---|
| *A61B 18/00* | (2006.01) | |
| *A61B 34/30* | (2016.01) | |
| *A61B 34/35* | (2016.01) | |

(52) U.S. Cl.
CPC .............. *A61B 34/30* (2016.02); *A61B 34/35* (2016.02); *A61B 2017/2933* (2013.01); *A61B 2017/2936* (2013.01); *A61B 2017/2947* (2013.01); *A61B 2018/00077* (2013.01); *A61B 2018/00083* (2013.01); *A61B 2018/00178* (2013.01); *A61B 2018/00595* (2013.01)

(58) Field of Classification Search
CPC .... A61B 2017/2933; A61B 2017/2936; A61B 2017/2947; A61B 2018/00077; A61B 2018/00083; A61B 2018/00178; A61B 2018/00595
USPC ......................................................... 606/32
See application file for complete search history.

(56) References Cited

U.S. PATENT DOCUMENTS

| | | | |
|---|---|---|---|
| 5,478,350 | A | 12/1995 | Kratsch et al. |
| 5,695,511 | A | 12/1997 | Cano et al. |
| 5,749,893 | A | 5/1998 | Vidal et al. |
| 5,843,122 | A | 12/1998 | Riza |
| 5,904,702 | A | 5/1999 | Ek et al. |
| 5,919,206 | A | 7/1999 | Gengler et al. |
| 6,193,718 | B1 | 2/2001 | Kortenbach et al. |
| 6,733,514 | B2 | 5/2004 | Miser |
| 8,333,780 | B1 | 12/2012 | Pedros et al. |
| 8,545,515 | B2 | 10/2013 | Prisco et al. |
| 8,771,270 | B2 | 7/2014 | Burbank |
| 9,498,242 | B2 | 11/2016 | Crews et al. |
| 10,716,617 | B2 | 7/2020 | Crews et al. |
| 2003/0191494 | A1 | 10/2003 | Gray et al. |
| 2006/0217706 | A1 | 9/2006 | Lau et al. |
| 2008/0167651 | A1 | 7/2008 | Tetzlaff et al. |
| 2010/0057085 | A1 | 3/2010 | Holcomb et al. |
| 2011/0184459 | A1 | 7/2011 | Malkowski et al. |
| 2011/0196419 | A1 | 8/2011 | Cooper |
| 2012/0078040 | A1 | 3/2012 | Suzuki et al. |
| 2013/0018373 | A1 | 1/2013 | Lau et al. |
| 2013/0023911 | A1 | 1/2013 | Esanu |
| 2014/0012290 | A1 | 1/2014 | Cooper et al. |
| 2014/0216187 | A1 | 8/2014 | Castro |
| 2020/0397502 | A1 | 12/2020 | Crews et al. |

FOREIGN PATENT DOCUMENTS

| | | |
|---|---|---|
| DE | 202004010780 U1 | 9/2004 |
| JP | H0617291 U | 3/1994 |
| JP | H08509635 A | 10/1996 |
| JP | H10502848 A | 3/1998 |
| JP | 2004524923 A | 8/2004 |
| JP | 2008534068 A | 8/2008 |
| JP | 2012501736 A | 1/2012 |
| JP | 2012045031 A | 3/2012 |
| WO | WO-9915089 A1 | 4/1999 |
| WO | WO-02080797 A1 | 10/2002 |
| WO | WO-2011033860 A1 | 3/2011 |
| WO | WO-2011097095 A1 | 8/2011 |

OTHER PUBLICATIONS

Extended European Search Report for Application No. 14768826.1, mailed on Oct. 7, 2016, 8 pages.
Extended European Search Report for Application No. 19151045.2, mailed on Mar. 29, 2019, 8 pages.
International Search Report and Written Opinion for Application No. PCT/US14/26137, mailed on Aug. 4, 2014, 14 pages (ISRG05020/PCT).
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

PROXIMAL ◄─────────► DISTAL

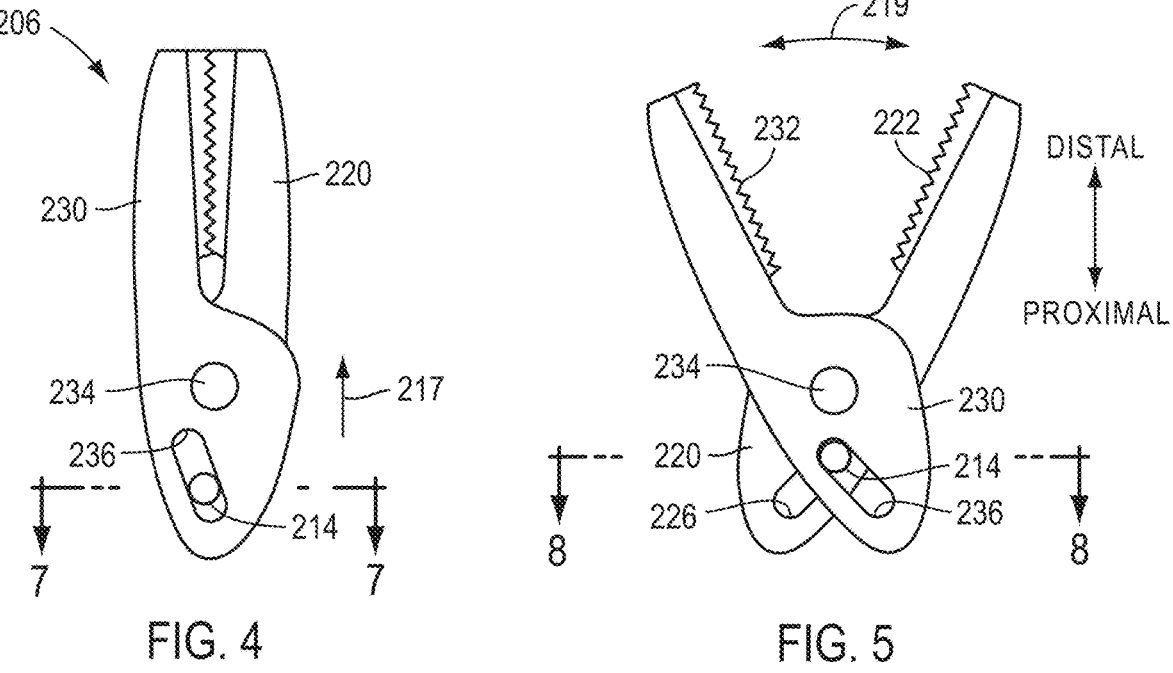
FIG. 4
FIG. 5
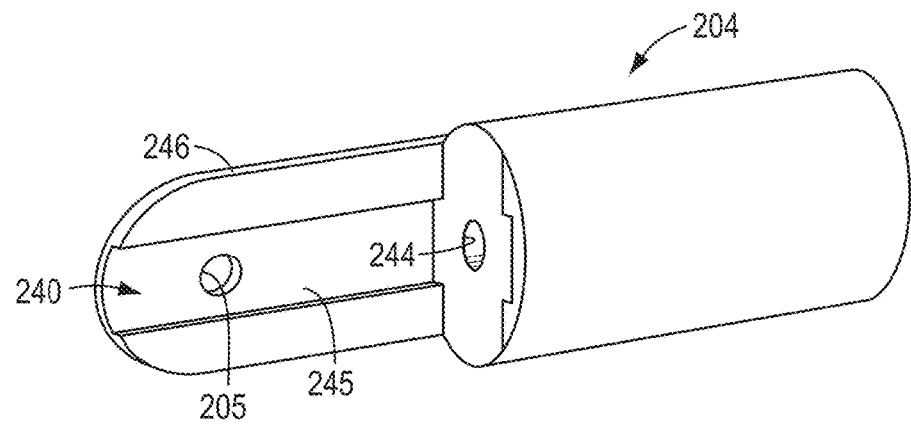
FIG. 6

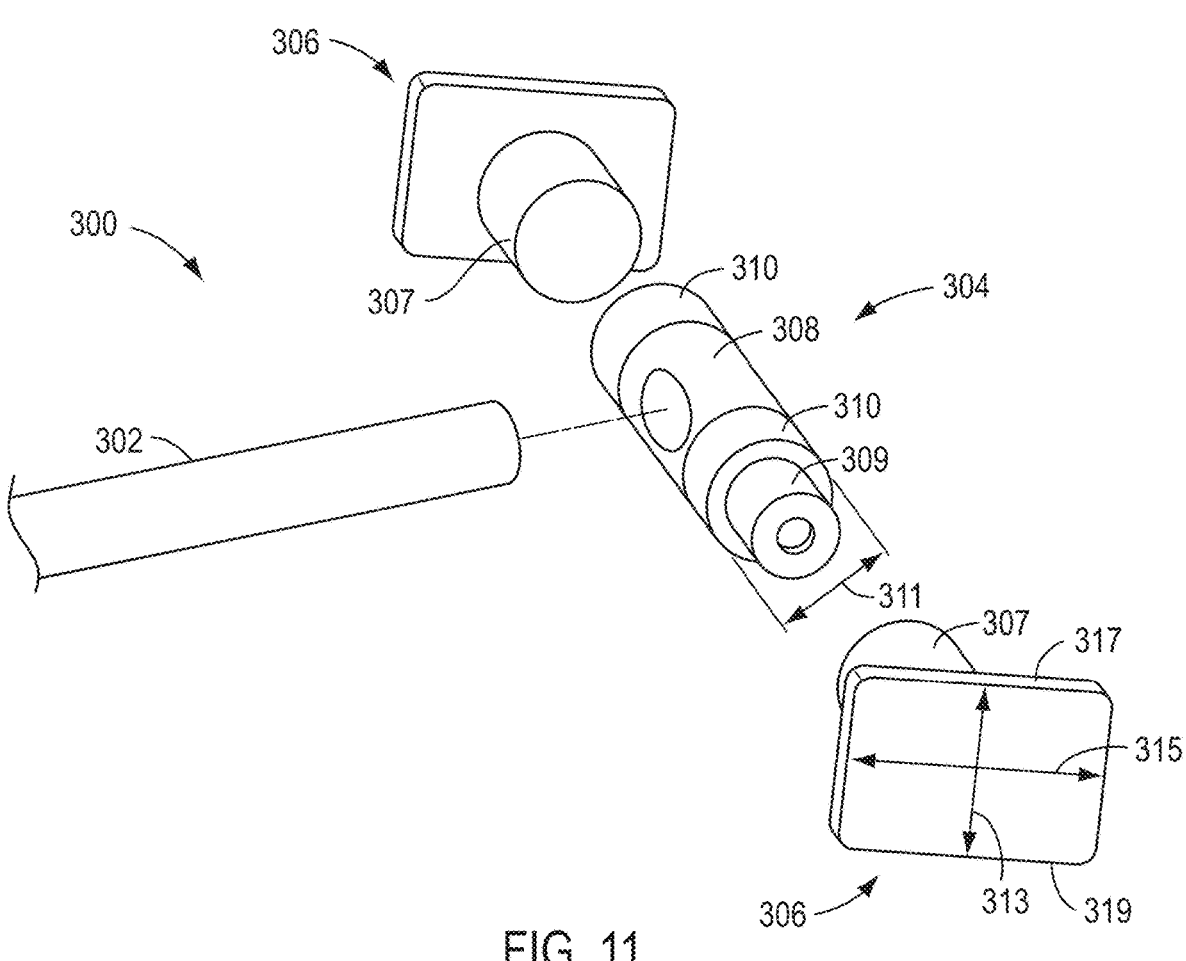
FIG. 11
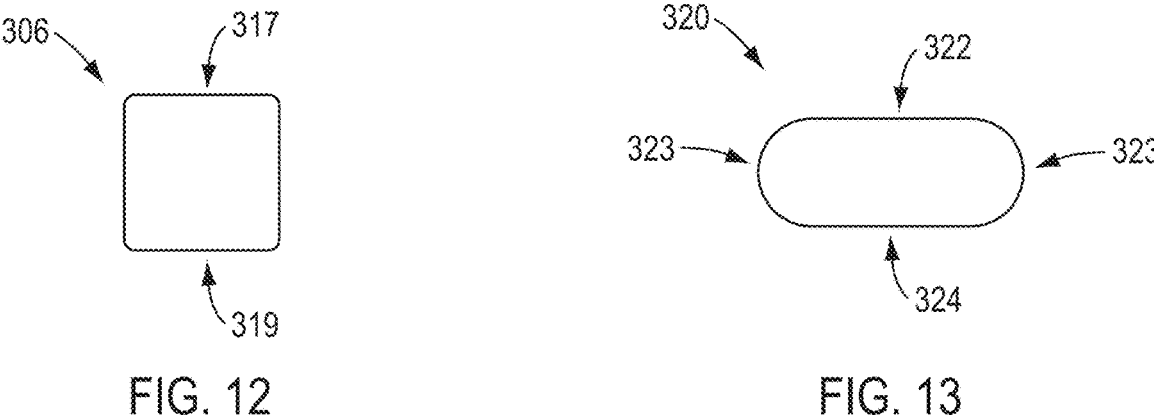
FIG. 12                                    FIG. 13

SURGICAL INSTRUMENT WITH ELECTRICAL CONNECTION, AND RELATED DEVICES, SYSTEMS, AND METHODS

This application is a continuation application of U.S. patent application Ser. No. 16/918,026, filed Jul. 1, 2020, which is a continuation application of U.S. patent application Ser. No. 15/348,127, filed Nov. 10, 2016 (now U.S. Pat. No. 10,716,617), which is a divisional application of U.S. patent application Ser. No. 14/209,043, filed on Mar. 13, 2014 (now U.S. Pat. No. 9,498,242), which claims the benefit of U.S. Provisional Application No. 61/803,046, filed on Mar. 18, 2013, each of which is incorporated by reference herein in its entirety.

TECHNICAL FIELD

Aspects of the present disclosure relate to a surgical instrument for a teleoperated (robotic) surgical system. Further aspects relate to a drive element for a surgical instrument and an electrical connection for a surgical instrument.

INTRODUCTION

Some minimally invasive surgical techniques are performed remotely through the use of teleoperated (robotically-controlled) surgical instruments (which may also be referred to as tools). In teleoperated surgical systems, surgeons manipulate input devices at a surgeon console, and those inputs are passed to a patient side cart that interfaces with one or more teleoperated surgical instruments. Based on the surgeon's inputs at the surgeon console, the one or more teleoperated surgical instruments are actuated at the patient side cart to operate on the patient, thereby creating a master-slave control relationship between the surgeon console and the surgical instrument(s) at the patient side cart.

Teleoperated surgical systems may have multiple arms to which surgical instruments may be coupled. The surgical instruments include end effectors used to perform surgical procedures. An end effector may be actuated by a drive element. Further, when the end effector is energized, such as for a cauterization procedure, the surgical instrument includes an electrical connection to provide electrical energy to the end effector. It is desirable to provide drive elements and electrical connections with enhanced durability while also performing their respective functions within the small space of a surgical instrument.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a surgical instrument comprises a shaft, an end effector connected to the shaft, and a push/pull drive element. The push/pull drive element comprises a head that extends perpendicular to a push/pull direction of the push/pull element. The head of the push/pull drive element may have end portions each having a cross-section that differs from a cross-section of a main portion of the head between the end portions.

In accordance with at least one exemplary embodiment, a surgical instrument may comprise a shaft, an end effector connected to the shaft, and a push/pull drive element. The push/pull drive element may include an engagement portion and an end portion connected to an end of the engagement portion. The engagement portion may be in contact with the end effector to actuate the end effector. The engagement portion may have a first width and the end portion may have a second width, wherein the second width is greater than the first width.

In accordance with at least one exemplary embodiment, a surgical instrument may comprise a shaft, an end effector connected to the shaft, at least one conduit to provide energy to the end effector, and a connector. The connector may electrically connect the at least one conduit to the end effector. The end effector may be in sliding contact with a portion of the connector.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

FIG. 4 is a side view of the end effector of FIG. 2, along line 4-4 of FIG. 2, the end effector being in a closed position.

FIG. 5 is a view of the end effector of FIG. 4 in an open position.

FIG. 6 is a cut-away view of an exemplary embodiment of a clevis of a surgical instrument in accordance with the present disclosure.

FIG. 11 is an exploded view of the push/pull drive element of FIG. 10.

FIG. 12 is an end view of the push/pull drive element of FIG. 10.

FIG. 13 is an end view of another exemplary embodiment of a push/pull drive element.

DETAILED DESCRIPTION

Figure 1:
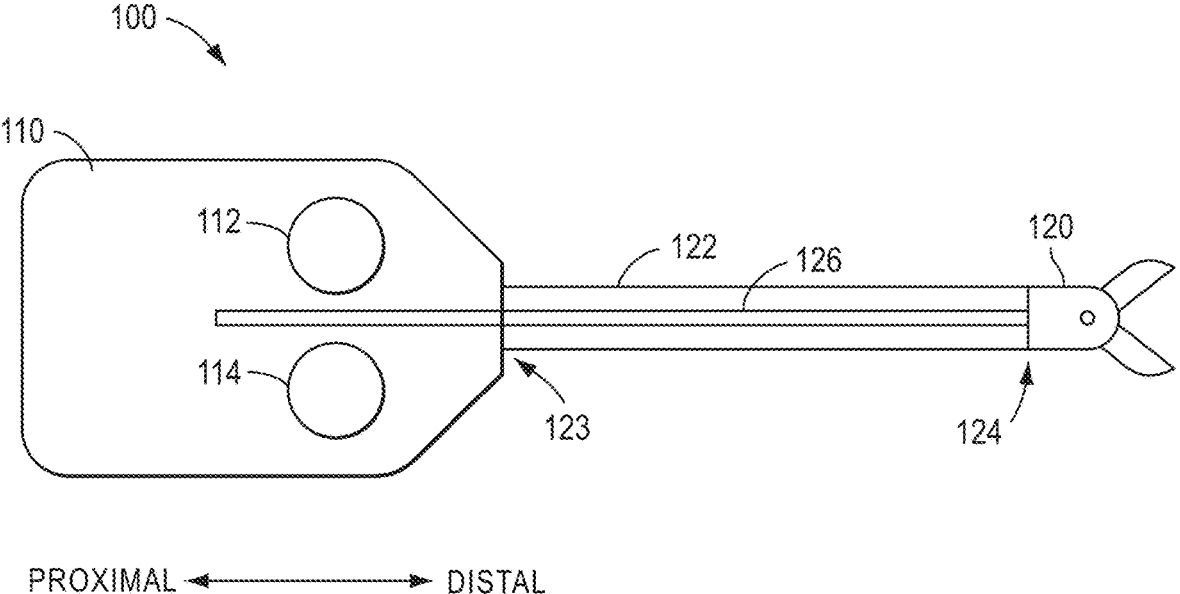
FIG. 1 is a top view of an exemplary embodiment of a surgical instrument including a force transmission mechanism.

Exemplary embodiments discussed herein regard a surgical instrument for a teleoperated surgical system. The surgical instrument may be relatively simple and inexpensive to manufacture, while providing a robust configuration resulting in a relatively durable instrument able to perform multiple functions within a relatively compact design.

This description and the accompanying drawings that illustrate exemplary embodiments should not be taken as limiting. Various mechanical, compositional, structural, electrical, and operational changes may be made without departing from the scope of this description and the invention as claimed, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent.

As used herein, the term "include" and its grammatical variants are intended to be non-limiting, such that recitation of items in a list is not to the exclusion of other like items that can be substituted or added to the listed items.

This description's terminology is not intended to limit the present disclosure or claims. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

Teleoperated surgery generally involves the use of a manipulator that has multiple manipulator arms. One or more of the manipulator arms often support a surgical instrument. One or more of the manipulator arms may be used to support a surgical image capture device, such as an endoscope (which may be any of a variety of structures such as a laparoscope, an arthroscope, a hysteroscope, or the like), or, optionally, some other imaging modality (such as ultrasound, fluoroscopy, magnetic resonance imaging, or the like). Typically, the manipulator arms will support at least two surgical tools corresponding to the two hands of a surgeon and one image capture device. Such teleoperated surgical systems are described in U.S. Pat. No. 8,545,515 entitled "Curved Cannula Surgical System," issued on Oct. 1, 2013, which is hereby incorporated by reference in its entirety.

Turning to FIG. 1, a side view of an exemplary embodiment of a surgical instrument 100 for a teleoperated surgical system is shown. Surgical instrument 100 may include a force transmission mechanism 110, a shaft 122 connected to force transmission mechanism 110 at a proximal end 123 of shaft 122, and an end effector 120 connected to a distal end 124 of shaft 122. Shaft 122 may be flexible. According to an exemplary embodiment, shaft 122 may have a diameter ranging from about 3 mm to about 15 mm. According to another exemplary embodiment, the diameter of shaft 122 may range, for example, from about 5 mm to about 8 mm. Surgical instrument 100 may include one or more members to translate force between force transmission mechanism 110 and end effector 120. For instance, one or more drive element(s) 126 may connect force transmission mechanism 110 to end effector 120 to provide actuation forces to end effector 120, such as by extending through an interior of shaft 122. By utilizing drive element(s) 126, force transmission mechanism 110 may actuate end effector 120 to, for example, control a wrist mechanism (not shown in FIG. 1) of instrument 100 and/or to control a jaw of end effector 120 (or other moveable part). Further, because end effector 120 may be fixed to shaft 122, force translated from force translation mechanism 110 to end effector 120 may in turn be translated to shaft 122, such as when force translation mechanism 110 actuates end effector 120 in a rolling motion. Drive element(s) 126 may be in the form of tension elements, such as when force transmission mechanism 110 is a pull-pull mechanism, or one or more drive element rods or push rods, such as when force transmission mechanism 110 is a push-pull mechanism, as described in U.S. Pat. No. 8,545,515.

Force transmission mechanism 110 may include one or more components to engage with a patient side cart of a teleoperated surgical system to translate a force provided by patient side cart to surgical instrument 100. According to an exemplary embodiment, force transmission mechanism 110 may include one or more interface disks 112, 114 that engage with a manipulator of a patient side cart, as described in U.S. Pat. No. 8,545,515. Thus, interface disks 112, 114 utilize actuation forces from a manipulator to actuate instrument 100. For instance, first disk 112 may be configured to provide a rolling motion to shaft 122 and provide a roll DOF for end effector 120, while second disk 114 may operate a jaw mechanism of end effector 120 to open and close. The force transmission mechanism may include other interface disks that actuate various other functionalities of a surgical instrument, as those having ordinary skill in the art are familiar with.

Figures 2, 3:
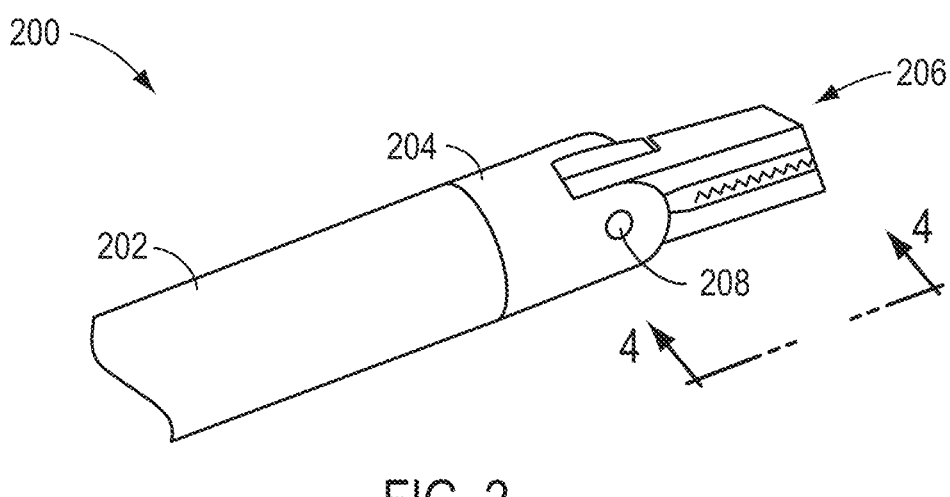
FIG. 2 is a partial perspective view of an exemplary embodiment of a surgical instrument having an end effector.
FIG. 3 is an exploded view of the surgical instrument of FIG. 2.

Turning to FIG. 2, an exemplary embodiment of a surgical instrument 200 for a teleoperated surgical system is shown that includes a shaft 202, clevis 204, and an end effector 206. According to an exemplary embodiment, surgical instrument 200 may include a wrist that couples the clevis 204 to the shaft 202, or surgical instrument 200 may be a non-wristed instrument. If surgical instrument 200 lacks a wrist, end effector 206 may be directly connected to clevis 204 and clevis 204 may be directly connected to shaft 202. As shown in FIG. 3, which is an exploded view of the exemplary embodiment of FIG. 2, end effector 206 may include a first jaw 220 and a second jaw 230. First jaw 220 may include a grip portion 222, a connection aperture 224, and an actuation aperture 226. Similarly, second jaw 230 may include a grip portion 232, a connection aperture 234, and an actuation aperture 236.

According to an exemplary embodiment, connection apertures 224, 234 may be used to connect jaws 220, 230 to clevis 204, which is in turn connected to shaft 202. For instance, as shown in the exemplary embodiment of FIGS. 2 and 3, a rivet or pin 208 may be inserted through connection apertures 224, 234 and through an aperture 205 in clevis 204 to connect jaws 220, 230 to clevis 204. Pin 208 may also serve as an axis of rotation about which jaws 220, 230 rotate when end effector 206 is actuated to open and close jaws 220, 230, which will be described below.

Surgical instrument 200 may include a mechanism to actuate end effector 206, such as to open and close jaws 220, 230. As shown in the exemplary embodiment of FIG. 3, surgical instrument may include a drive element 210 connected to end effector 206. A proximal end (not shown) of drive element 210 may be connected to a manipulator (not shown) of a teleoperated surgical system that provides motive force to drive element 210. For instance, drive element 210 may be a push/pull drive element rod that is pushed or pulled along direction 213 in FIG. 3 by a motive force provided by the manipulator to actuate end effector 206.

A distal end 215 of drive element 210 may be connected to end effector 206 to translate the motive force from the manipulator to the jaws 220, 230. According to an exemplary embodiment, distal end 215 of drive element 210 may include a first projection 212 connected to jaw 220 and a second projection 214 connected to jaw 230. For instance, jaw 220 may include an actuation aperture 226 that first projection 212 is inserted into and jaw 230 may include an actuation aperture 236 that second projection 214 is inserted into. Actuation apertures 226, 236 may be in form of, for example, elongated slots, such as rectangular or oval slots that projections 212, 214 may be inserted into. Thus, as drive element 210 is pushed or pulled along direction 213 in FIG. 3, projections 212, 214 may slide within actuation apertures 226, 236, causing jaws 220, 230 to pivot about pin 208.

Turning to FIG. 4, a side view of end effector 206 is shown along line 4-4 in FIG. 2 but without clevis 204 and pin 208. In the exemplary embodiment of FIG. 4, the jaws 220, 230 of end effector 206 are in a closed state. Although drive element 210 is not shown in FIG. 4, second projection 214 is shown within actuation slot 236 of jaw 230. When drive element 210 is pushed in direction 217 in FIG. 4, second projection 214 is forced upwards. Consequently, jaws 220, 230 rotate and pivot about pin (not shown) located in connection aperture 234 in direction 219 in FIG. 5, causing jaws 220, 230 to separate and open.

Surgical instrument 200 may include one or more features to assist with the movement of drive element 210 during actuation of end effector 206, such as between the closed and open states shown in the exemplary embodiments of FIGS. 4 and 5, respectively. According to an exemplary embodiment, clevis 204 may include one or more features to assist with the movement of drive element 210. Turning to FIG. 6, a cut away view of an exemplary embodiment of clevis 204 is provided. Clevis 204 includes a sidewall 246 that forms an outer surface of clevis 204 and in FIG. 6 a portion of sidewall 246 has been removed to show internal features of clevis 204.

Clevis 204 may include a lumen 244 for passage of drive element 210 through clevis 204 and an aperture 205 for a pin 208 to connect jaws 220, 230 of an end effector 206, as discussed above in regard to the exemplary embodiment of FIG. 3. According to an exemplary embodiment, clevis 204 may include other lumens for other components, such as, for example, conduits to provide energy to end effector 206 (e.g., electrical wires) and/or additional actuation components (e.g., an actuation element for an additional degree of freedom for surgical instrument or for a component, such as a knife).

To assist with the movement of drive element 210, clevis 204 may include one or more features to interact with the projections 212, 214 of drive element 210. For instance, clevis 204 may include a groove 240 in the sidewall 246, as shown in the exemplary embodiment of FIG. 6. According to an exemplary embodiment, groove 240 may have a finite depth and a bottom surface 245, as shown in FIG. 6. However, the configuration of groove 240 is not limited to such a geometry and groove 240 may instead be provided as a slot (not shown) that passes completely through sidewall 246 of clevis 204. One or more projections 212, 214 of drive element 210 may be configured to extend into groove 240 so that when drive element 210 is moved to actuate end effector 206, groove 240 supports a projection 212, 214. In other words, one or more projections 212, 214 of drive element 210 may have a length sufficient to extend through jaws 220, 230 (such as through actuation apertures 226, 236) and into groove 240 in sidewall 246.

Figure 7:
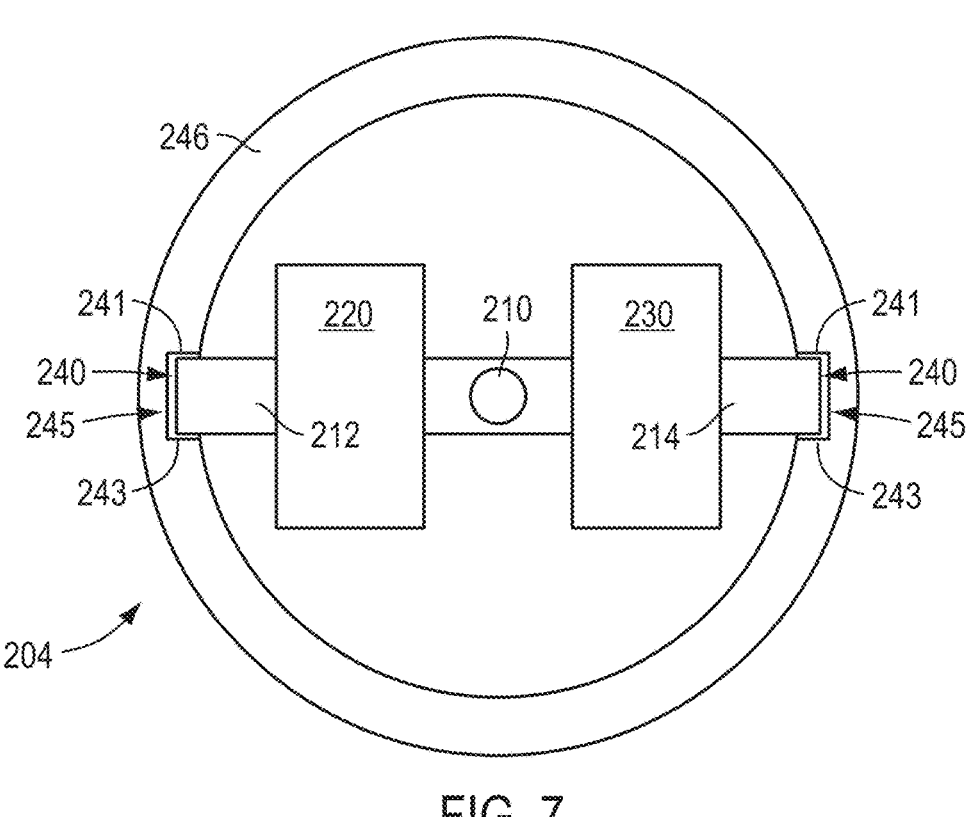
FIG. 7 is a cross-section view along line 7-7 of FIG. 4 but with an exemplary embodiment of a clevis also shown.
Figure 8:
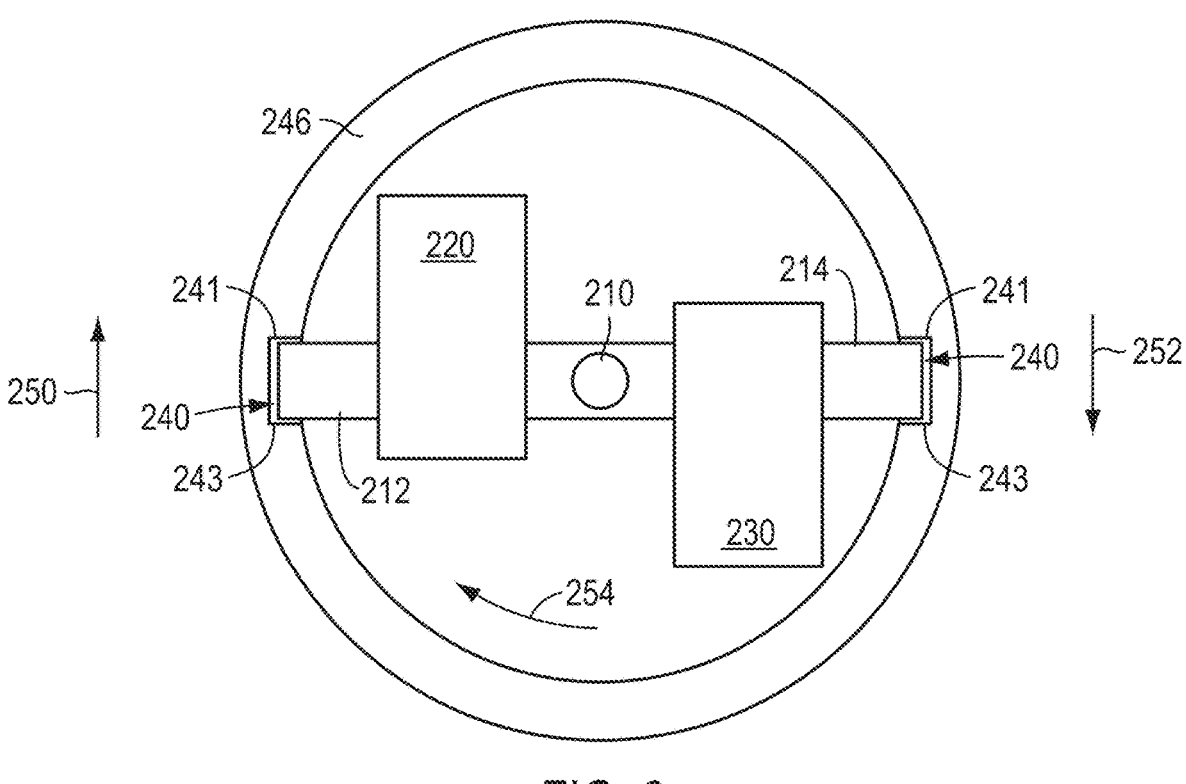
FIG. 8 is a cross-sectional view along line 8-8 of FIG. 5 but with an exemplary embodiment of a clevis also shown.
Figure 9:
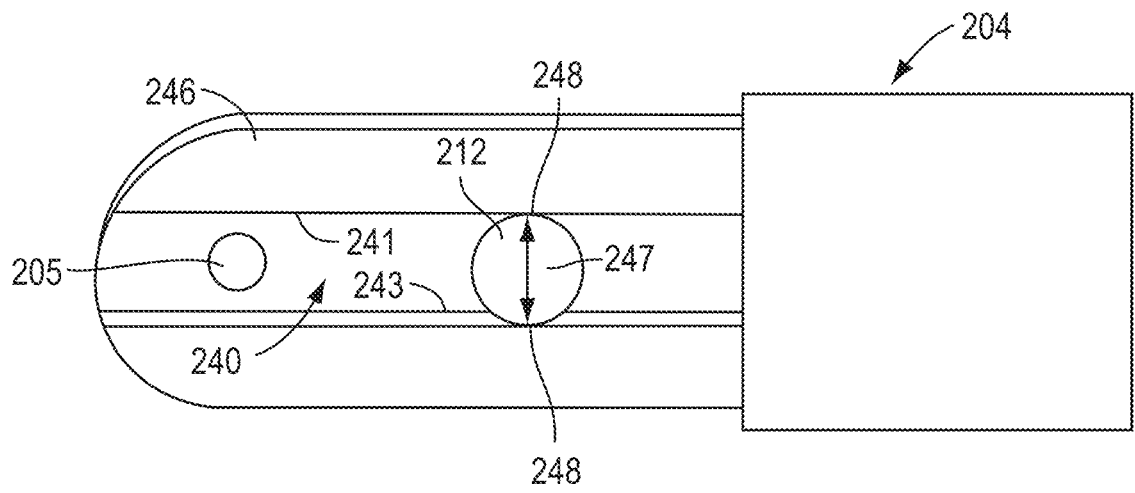
FIG. 9 is a cut-away view of an exemplary embodiment of a clevis and an end of a projection of a drive element located within a groove of the clevis.

Turning to FIG. 7, a cross-section view is shown along line 7-7 of FIG. 4 is shown but with clevis 204 also provided. FIG. 8 depicts a cross-sectional view along line 8-8 of FIG. 5 but with clevis also provided. As shown in the exemplary embodiment of FIG. 7, clevis 204 may include two grooves 240; one for each projection 212, 214 of drive element 210. In addition, grooves 240 may be opposed to one another, as shown in FIG. 7. Because projections 212, 214 of drive element 210 are placed within grooves 240, when drive element 210 is moved to actuate an end effector 206 (e.g., by moving drive element 210 in and out of the page of FIG. 7), grooves 240 support and/or guide the movement of projections 212, 214 and thus drive element 210. For instance, at least one of sidewalls 241, 243 of groove 240 may contact projections 212, 214 as drive element 210 is moved and projections 212, 214 slide back and forth within groove 240. According to an exemplary embodiment, a bottom surface 245 of groove 240 may be in contact with projections 212, 214 to support projections 212, 214, either alternatively or in addition to contact with one or more sidewalls 241, 243. Turning to FIG. 9, a cut-away view of an exemplary embodiment of clevis 204 is shown, which is similar to the view of FIG. 6, except that the end of projection 212 is shown within groove 240. As shown in the exemplary embodiment of FIG. 9, projection 212 may contact sidewalls 241, 243 of groove 240, such as at contact portions 248, so that projection 212 is supported by groove 240. Because projections 212, 214 have a substantially circular cross section, even at the ends of projections 212, 214 that fit within grooves 240, contact portions 248 may be characterized by contact between a circle and a planar surface. For instance, contact portions 248 may be a substantially tangential contact portion between projections 212, 214 and sidewalls 214, 243 of groove 240. In other words, contact portions 248 may have a shape of line or a point. Thus, all of the stress transmitted between projections 212, 214 and sidewalls 241, 243 is concentrated to relatively small areas.

When drive element 210 is moved to actuate an end effector 206 to open and close jaws 220, 230, portions of jaws 220, 230 may move apart from one another. This is also demonstrated in FIGS. 7 and 8. In FIG. 7, jaws 220, 230 are in a closed position, as shown in the exemplary embodiment of FIG. 4. In FIG. 8, jaws 220, 230 have been moved to an open position due to the movement of drive element 210, as shown in the exemplary embodiment of FIG. 5. In particular, the proximal ends of jaws 220, 230 may move in different directions when jaws 220, 230 move to an open position, as shown in the exemplary embodiment of FIG. 5. This is also demonstrated in FIG. 8, which shows that the end of jaw 220 has moved in direction 250 relative to FIG. 7 and that the end of jaw 230 has moved in direction 252 relative to FIG. 7.

Because of the motions of jaws 220, 230 in respective directions 250, 252, a torque is exerted upon drive element 210 in direction 254 shown in the exemplary embodiment of FIG. 8. Torque in direction 254 causes drive element 210 to twist, resulting in projection 212 exerting force against sidewall 243 of one groove 240 and projection 214 exerting force against sidewall 241 of another groove 240. Further, due to the geometry of contact portions 248 between projections 212, 214 and sidewalls 241, 243 of grooves 240, such as line or point contact, the force exerted between projections 212, 214 and sidewalls 241, 243 is limited to small areas. As a result, grooves 240 may permanently deform and/or wear as projections 212, 214 slide back and forth within grooves 240 and press against sidewalls 241, 243. According to an exemplary embodiment, jaws 220, 230 may move in opposite directions to directions 250, 252 shown in the exemplary embodiment of FIG. 8 when jaws 220, 230 are actuated to a closed position, which may result in a torque and twisting motion in a direction opposite to direction 254 in FIG. 8.

According to an exemplary embodiment, clevis 204 may be made from a non-metallic material. For instance, clevis 204 may be made of a plastic, such as, for example polyether ether ketone (PEEK), including glass filled PEEK. When clevis 204 is made of a non-metallic material, for example, a plastic material, permanent deformation and/or wear may occur on the surfaces of grooves 240, such as sidewalls 241, 243. In addition, forces between projections 212, 214 and sidewalls 241, 241 may even be sufficient for projections to pop out of grooves 240 when drive element 210 is twisted in direction 254, particularly when sidewalls 241, 243 have become worn.

In view of these considerations, it may be desirable to provide a surgical instrument with enhanced durability. In particular, it may be desirable to provide a surgical instrument with one or more features to support and/or guide the movement of a drive element for an end effector that have enhanced durability, such as by enhancing the distribution of force between the drive element and another component of the surgical instrument.

Figure 10:
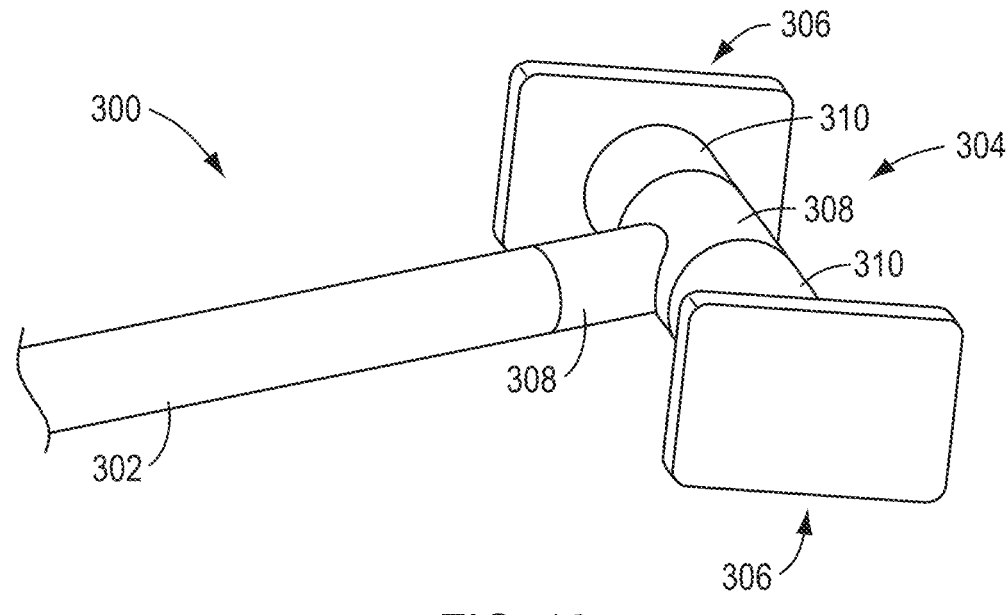
FIG. 10 is a partial perspective view of an exemplary embodiment of a push/pull drive element.

Turning to FIG. 10, a perspective view of an exemplary embodiment of a push/pull drive element 300 is shown. Push/pull drive element 300 may be, for example, a push rod, a wire, a cable, or other structure known by one of ordinary skill in the art for use as a push/pull drive element. For instance, push/pull drive element may be an element with sufficient columnar compressibility to transmit an axial pushing force applied to the push/pull drive element. Push/pull drive element 300 may be used according to the same functions as drive element 210 described above for the exemplary embodiments of FIGS. 2-9. As shown in FIG. 10, push/pull drive element 300 may include a shaft 302 connected to a head 304. Head 304 may include, for example, a cross shaft 309 and end portions 306, as shown in FIG. 11. Cross shaft 309 may also be referred to, for example, as a main portion of head 304. Head 304 may be formed from separate pieces, such as cross shaft 309 and end portions 306, as shown in the exemplary embodiment of FIGS. 10 and 11, or head 304 may be provided with a single piece construction by providing cross shaft 309 and end portions 306 as a single piece. According to an exemplary embodiment, portions of push/pull drive element 300, such as shaft 302 and cross shaft 309 and end portions 306, may be made of a metal. For example, portions of push/pull drive element 300 may be made of a wear resistant stainless steel alloy, such as Nitronic® 60.

According to an exemplary embodiment, push/pull drive element 300 may include an insulative material 308, such as when push/pull drive element 300 is used in a surgical instrument is energized, as will be discussed below. Insulative material 308 may be a material that minimizes arcing and electrical conductivity, such as, for example, a plastic material. As shown in the exemplary embodiment of FIG. 10, insulative material 308 may be provided on at least a portion of cross shaft 309 and shaft 302. For instance, insulative material 308 may be provided on at least one of cross shaft 309 and shaft 302 by overmolding the insulative material 308.

According to an exemplary embodiment, cross shaft 309 includes engagement portions 310 that engage with portions of an end effector when push/pull drive element 300 is moved to actuate the end effector. For instance, engagement portions 310 may be configured to engage actuation apertures 226, 236 of jaws 220, 230 of end effector 206, as described above in the exemplary embodiments of FIGS. 2-5, to actuate end effector 206 when push/pull drive element 300 is moved. According to an exemplary embodiment, engagement portions 310 may have a circular cross-section, like projections 212, 214 of the exemplary embodiments of FIGS. 2-8. Further, engagement portions 310 of cross shaft 309 may have a diameter 311 (see FIG. 11)

substantially the same as diameter 247 of projections 212, 214 (see FIG. 9). However, the diameter 311 of engagement portions 310 need not be substantially the same diameter 247 of projections 212, 214, but instead may be different. For instance, the diameter 311 of engagement portions 310 may be smaller than the diameter 247 of projections 212, 214, according to an exemplary embodiment.

According to an exemplary embodiment, engagement portions 310 may have a non-circular cross-section. For instance, a cross-sectional shape of engagement portions 310 may include one or more flat surface portions (not shown). One or more flat surface portions may be provided to increase the contact area between engagement portions 310 and actuation apertures 226, 236 of jaws 220, 230, such as to increase the distribution of forces exerted between engagement portions 310 and jaws 220, 230. According to an exemplary embodiment, actuation apertures 226, 236 of jaws 220, 230 may have a different shape than the shape shown in the exemplary embodiment of FIGS. 2 and 3. For instance, actuation apertures 226, 236 may be curved, instead of being straight as shown in FIGS. 2 and 3. For example, actuation apertures 226, 236 may be curved so that actuation apertures 226, 236 are either convex or concave in shape relative to connection apertures 224, 234 in the exemplary embodiment of FIG. 3.

End portions 306 of push/pull drive element 300 may be configured to enhance the distribution of forces between end portions 306 and other components of a surgical instrument, such as a clevis. As shown in the exemplary embodiment of FIGS. 10 and 11, end portions 306 may be larger than engagement portions 310 of cross shaft 309. For instance, engagement portions 310 may have a diameter or width 311, while end portions 306 may have a width 313 or 315 that is larger than the width 311 of engagement portions 310. If dimensions 313, 315 of end portions 306 are not equal or substantially equal, the width of end portions 306 may be the larger of dimensions 313, 315, according to an exemplary embodiment. For instance, when dimension 315 of end portion 306 is larger than dimension 313, dimension 315 is the width of end portions and is also larger than the width 311 of engagement portions 310. According to an exemplary embodiment, a ratio of dimension 315 to diameter 311 is greater than 1. For example, a ratio of dimension 315 to diameter 311 ranges from, for example, about 1.1 to about 1.3. According to an exemplary embodiment, dimension 315 may have a length of, for example, about 0.075 inches while diameter 311 is, for example, about 0.061 inches.

End portions 306 of push/pull drive element 300 may have a cross-section with various shapes. As shown in the exemplary embodiments of FIGS. 10 and 11, end portions 306 may have a rectangular shape. As shown in the exemplary embodiment of FIG. 12, end portions 306 may have a square shape. According to another exemplary embodiment, an end portion 320 may have an oval shape, as shown in FIG. 13. The oval shape may include flat surfaces 322, 324 and rounded ends 323, as shown in the exemplary embodiment of FIG. 13. However, the cross-sectional shape of end portions of a push/pull drive element is not limited to the exemplary embodiments of FIGS. 10-13 and other shapes may be utilized.

According to an exemplary embodiment, a cross-sectional shape of an end portion of a push/pull drive element includes one or more flat surface portions. As shown in the exemplary embodiments of FIGS. 11 and 12, end portions 306 may include flat surface portions 317, 319. Further, an end portion 320 having an oval shape or other non-rectangular or non-square shape may have flat surface portions 322, 324, as shown in the exemplary embodiment of FIG. 13. According to an exemplary embodiment, flat surface portions may be opposite to one another and substantially in planes that are parallel to the elongated direction of the groove 240 of the clevis, as shown in the exemplary embodiments of FIGS. 11-13.

By providing end portions 306 with a cross-section that is enlarged relative to that of the cross shaft 309, providing end portions 306 having a shape described above, and/or providing end portions 306 having at least one flat surface portion in a plane parallel to the elongated direction of the groove 240 of the clevis, a contact area between end portions 306 and a clevis of a surgical instrument may be increased. This in turn may enhance the distribution of forces between end portions 306 and the clevis.

Figures 14, 15:
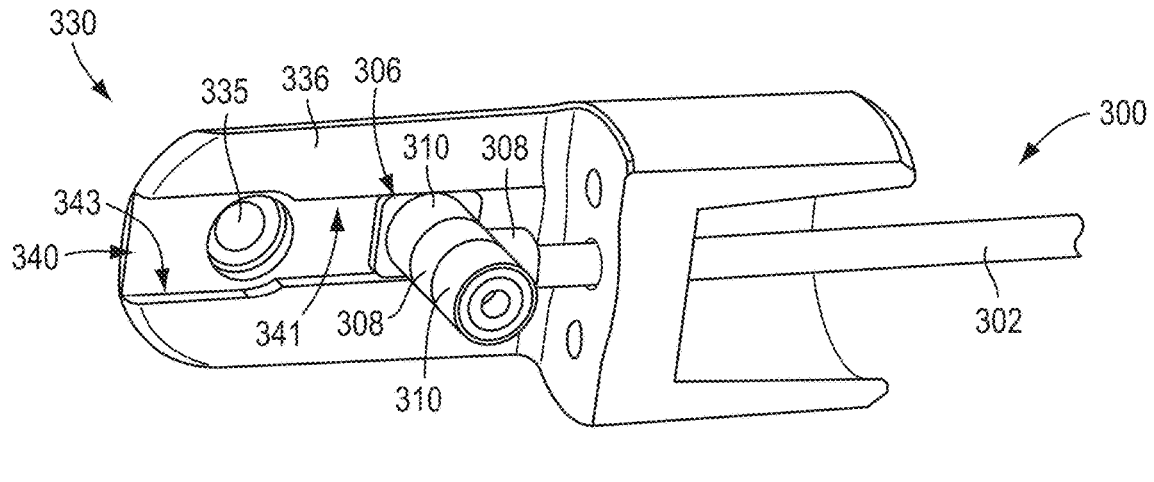
FIG. 14 is a partial cut-away view of an exemplary embodiment of a surgical instrument clevis and a push/pull drive element.
FIG. 15 is a partial cut-away view of an exemplary embodiment of a clevis and an end of a projection of a push/pull drive element.

Turning to FIG. 14, a cut away view of a clevis 330 is provided to show internal features of clevis 330, including groove 340 formed in a sidewall 336 of clevis 330. Clevis 330 may further include an aperture 335 for a pin (not shown) to connect the jaws of an end effector and groove 340 may include sidewalls 341, 343. As shown in the exemplary embodiment of FIG. 14, an end portion 306 of a push/pull drive element 300 may be placed within groove 340 so that groove 340 supports and/or guides end portion 306 as push/pull drive element 300 moves back and forth to actuate an end effector. In particular, the one or more surface portions of end portion 306 may be in contact with one or more surfaces of groove 340. Turning to FIG. 15, which is side view of clevis 340 and push/pull drive element 300, with an end portion 306 of push/pull drive element 300 located within groove 340, surface portions 317, 319 of end portion 306 may engage one or both of sidewalls 341, 343 of groove 340 via contact portions 350. According to an exemplary embodiment, surface portions 317, 319 may be flat. Because end portion 306 has one or more surface portions 317, 319, contact portions 350 between end portion 306 and sidewalls 341, 343 of groove 340 are not limited to point contacts or approximately tangential contacts, as discussed above in regard to the exemplary embodiment of FIG. 9, but instead provide relatively large contact areas over which the forces exerted between end portion 306 and groove 340 may be distributed. As a result, the forces are not concentrated to a small area, which may lead to permanent deformation and/or increased wear rates. Further, end portions 306 of push/pull drive element 300 have enhanced resistance to the forces exerted when push/pull drive element 300 actuates an end effector and is subjected to twisting, as described above in regard to the exemplary embodiment of FIGS. 7 and 8.

Figure 16:
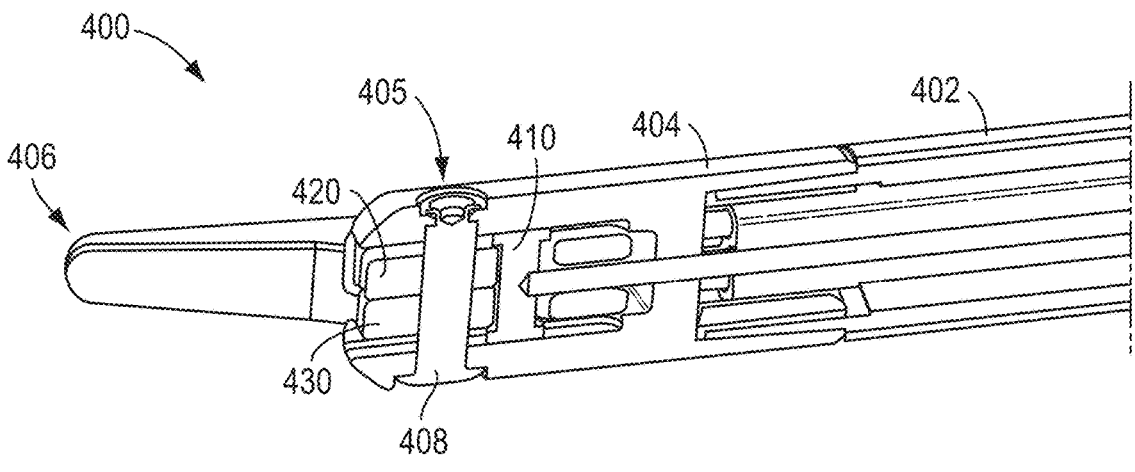
FIG. 16 is a partial cut-away view of an exemplary embodiment of a non-energized surgical instrument.
Figure 17:
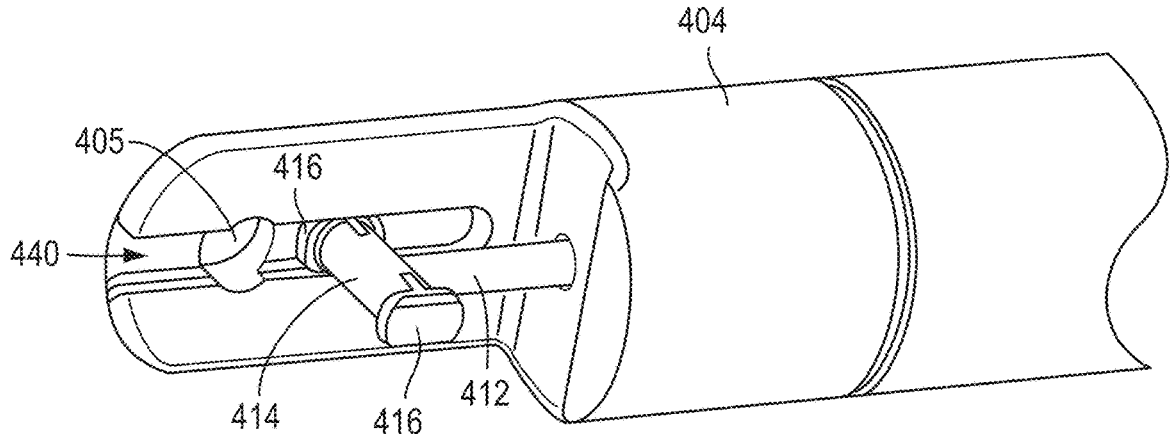
FIG. 17 is a cut-away view of an exemplary embodiment of a surgical instrument clevis and a push/pull drive element.

As described above with regard to the exemplary embodiments of FIGS. 10-14, push/pull drive element 300 may include an insulative material 308, particularly when push/pull drive element 300 is used in an energized surgical instrument. However, the exemplary embodiments described herein are not limited to energized surgical instruments and a push/pull drive element may be used in a non-energized surgical instrument. Turning to FIG. 16, a cut-away view of a non-energized surgical instrument 400 is shown. Surgical instrument 400 may include a shaft 402, clevis 404, end effector 406, and a push/pull drive element 410. End effector 406 may include jaws 420, 430 that may be connected to clevis 404 by a pin 408 inserted through an aperture 405. Push/pull drive element 410 may be configured according to the exemplary embodiments of FIGS. 10-15 except that push/pull drive element 410 does not include insulative material 308 because surgical instrument 400 is not energized. As shown in FIG. 17, which shows a cut-away view of clevis 404, push/pull drive element 410 may include a shaft 412, one or more engagement portions 414 (such as, for example, engagement portions 414 provided by a cross shaft, as discussed above in regard to FIG. 11), and one or more end portions 416. End portion 416 may be inserted within a groove 440 of clevis 404, as discussed above in regard to the exemplary embodiments of FIGS. 10-15, so that end portion 416 is guided and/or supported when push/pull drive element 410 moves back and forth to actuate end effector 406.

Due to the shape and size of end portions of a push/pull drive element as described in the exemplary embodiments of FIGS. 10-17, the amount of contact area between the end portions and a clevis groove is significantly increased. Thus, the end portions may advantageously enhance the distribution of force exerted between the end portions and grooves of a clevis. As a result, end portions of a push/pull drive element may counteract torque and a twisting motion applied to the push/pull drive element during actuation of an end effector, which may otherwise lead to deformation or wear of the clevis groove or the push/pull drive element popping out of the clevis groove. In particular, end portions of a push/pull drive element may minimize or reduce permanent deformation or wear of a groove of a clevis made of a non-metallic material, such as a plastic.

When a surgical instrument is energized, an electrical connection is provided between an end effector of the surgical instrument and one or more conduits providing electrical energy to the end effector. However, due to movements of the end effector, providing and maintaining a connection between the one or more conduits and the end effector may be difficult. Further, due to the small size of a surgical instrument and the limited about of space within a surgical instrument, the level of difficultly of providing a connection that is functional and durable is relatively high. For instance, an outer diameter of a surgical instrument may be, for example, approximately 5 mm.

Figure 18:
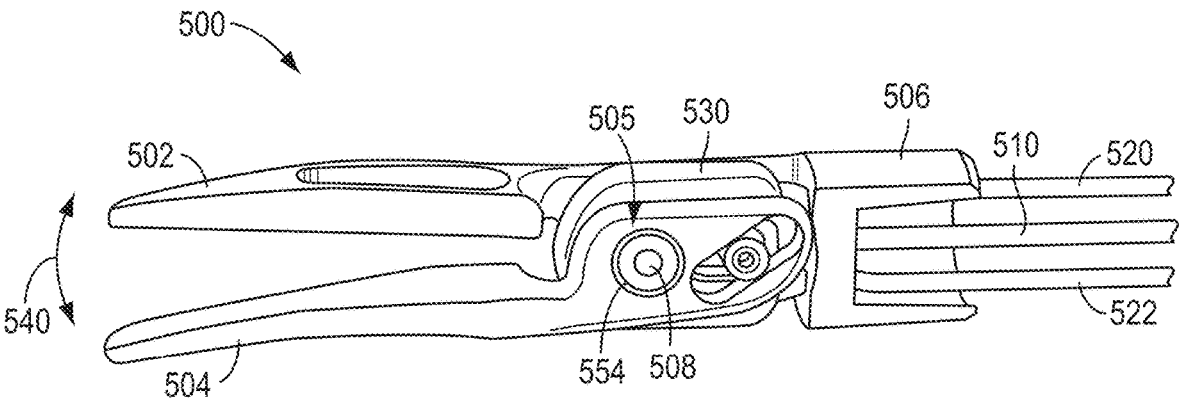
FIG. 18 is a partial side cut-away view of an exemplary embodiment of a surgical instrument.
Figure 19:
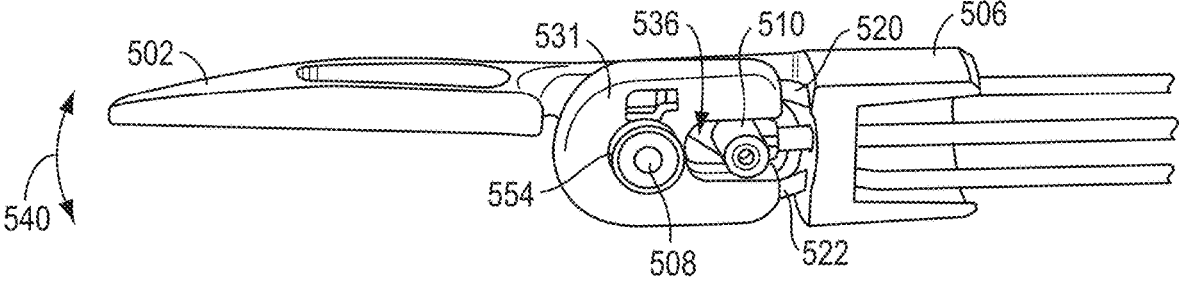
FIG. 19 is a partial side cut-away view of the surgical instrument of FIG. 18 with a jaw removed.

Turning to FIG. 18, an exemplary embodiment of a surgical instrument 500 is shown that includes jaws 502, 504 connected via a pin 508, a clevis 506, and a push/pull drive element 510. Push/pull drive element 510 may be configured according to the exemplary embodiments of FIGS. 10-17. According to an exemplary embodiment, surgical instrument 500 may further include a connector assembly 530 to connect one or more conduits 520, 522 to jaws 502, 504. Conduits 520, 522 may provide energy to jaws 502, 504, such as, for example electrical energy, to energize jaws 502, 504. FIG. 19 shows surgical instrument 500 with jaw 504 removed so that components of surgical instrument 500 may be more easily viewed, such as connector assembly 530. Surgical instrument 500 may further include a shaft (not shown) connected to clevis 506 and covering conduits 520, 522.

When jaws 502, 504 are actuated, jaws 502, 504 move relative to other components of surgical instrument 500. For instance, jaws 502, 504 may pivot in direction 540 relative to pin 508, as shown in the exemplary embodiments of FIGS. 18 and 19. Due to the movement of jaws 502, 504, providing a connection between conduits 520, 522 and jaws 502, 504 can be challenging. For instance, if conduits 520, 522 are directly connected to jaws 502, 504, at least a portion of conduits 520, 522 may move when jaws 502, 504 move, which may lead to challenges in providing a durable connection between jaws 502, 504 and conduits.

Figure 20:
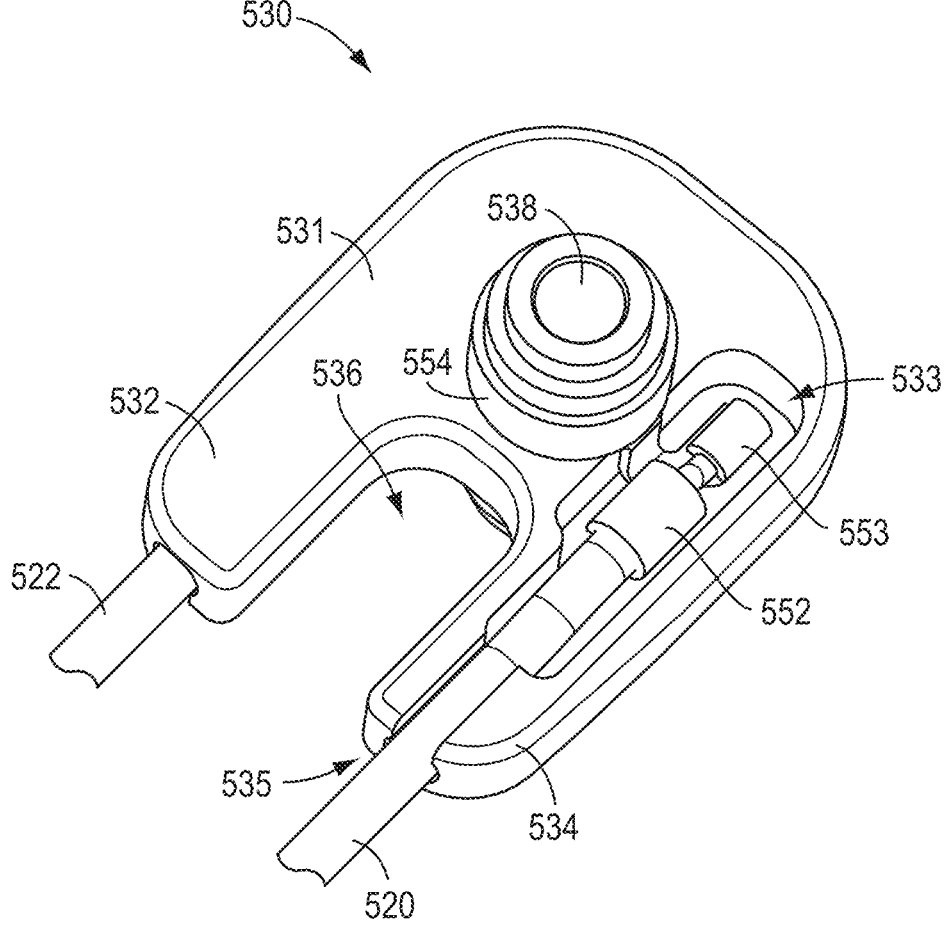
FIG. 20 is a perspective view of an exemplary embodiment of a connector assembly.

Turning to FIG. 20, an exemplary embodiment of a connector assembly 530 is shown, which includes a body 531. Connector assembly 530 may provide a connection between one or more conduits 520, 522 and an end effector, such as jaws 502, 504, so that energy (e.g., electrical energy) may be provided from the one or more conduits 520, 522 to the end effector. Thus, connector assembly 530 may provide an electrical connection between one or more conduits 520, 522 and an end effector, according to an exemplary embodiment. According to an exemplary embodiment, body 531 may be made of an insulative material, such as an electrically insulative material. For example, body 531 may be made of a plastic, such as, for example, a polyphthalamide (PPA) (e.g., Amodel®, which is sold by Solvay Advanced Polymers, L.L.C.). Body 531 may be used, for instance, to provide a structural support for a connection between one or more conduits 520, 522 and jaws 502, 504 while substantially insulating components of surgical instrument 500 from the energy connected between the one or more conduits 520, 522 and jaws 502, 504. As shown in the exemplary embodiment of FIG. 20, body 531 may be approximately U-shaped and include a first leg 532 and a second leg 534. Further, legs 532, 534 may be separated by a gap 536, as shown in the exemplary embodiment of FIG. 20. Gap 536 may, for example, provide space for movement of push/pull drive element 510 within body 531, as shown in the exemplary embodiment of FIG. 19, such as when push/pull drive element 510 is moved to actuate jaws 502, 504. Body 531 may further include a lumen 538 that pin 508 may be inserted through, as shown in the exemplary embodiment of FIGS. 18 and 19.

According to an exemplary embodiment, legs 532, 534 of body may include a structure to receive conduits 520, 522. For instance, leg 534 may include a cavity 533 to receive conduit 520, as shown in the exemplary embodiment of FIG. 20. Cavity 533 may be open, as shown in the exemplary embodiment of FIG. 20, or cavity may be at least partially covered. Conduit 520 may be received in cavity 533 by, for example, inserting conduit 520 through an aperture 535 in leg 534. Leg 532 may be configured according to any of the above exemplary embodiments discussed for leg 534.

Figure 21:
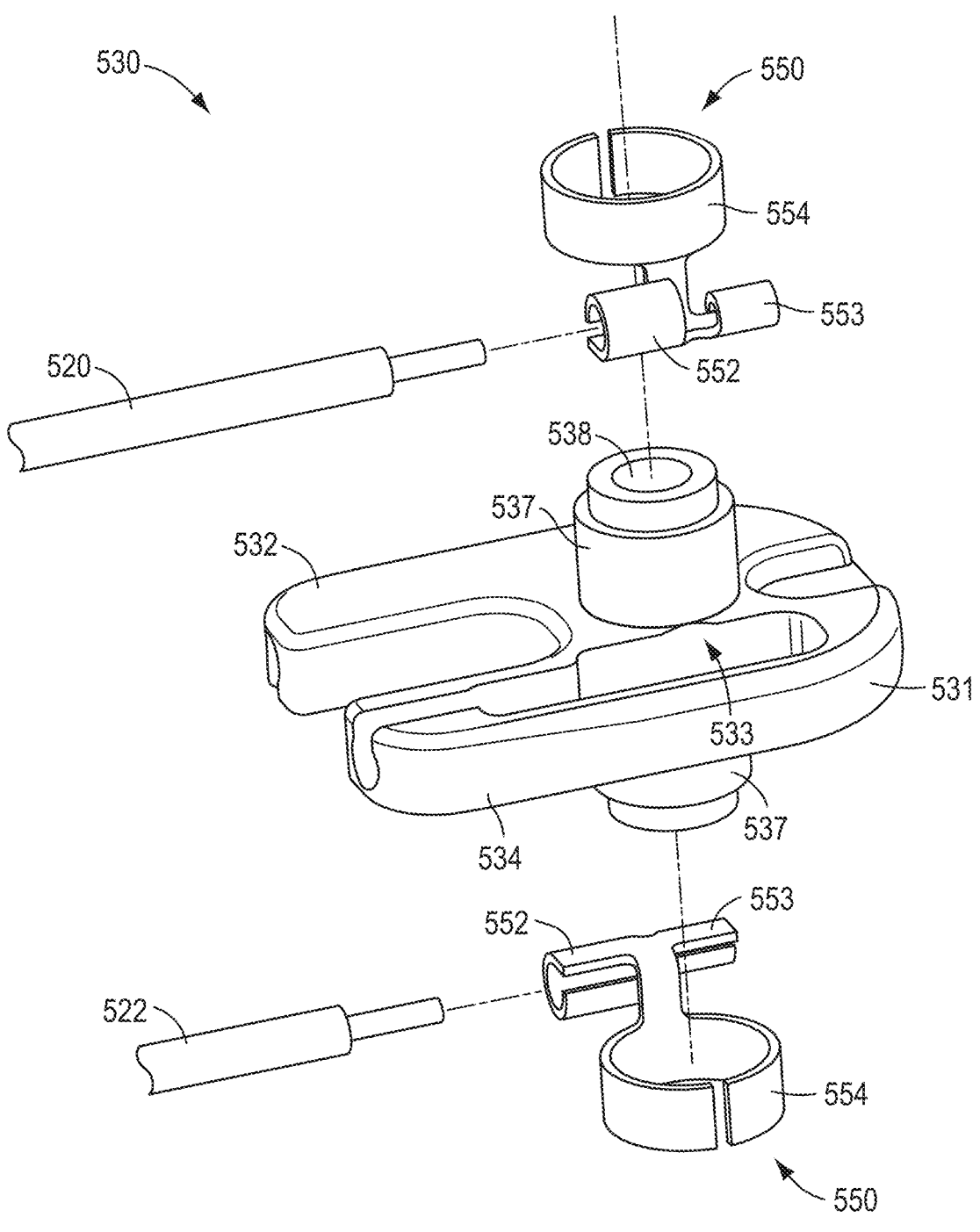
FIG. 21 is an exploded view of the connector assembly of FIG. 20.

As shown in FIG. 21, which is an exploded view of the exemplary embodiment of connector assembly 530 of FIG. 20, connector assembly 530 may further include one or more connector portions 550. According to an exemplary embodiment, connector assembly 530 may include a connector portion 550 for each conduit. For instance, connector assembly 530 may include a connector portion 550 for each of conduits 520, 522, as shown in FIG. 21. Connector portions 550 may be attached to body 531. As shown in the exemplary embodiment of FIG. 21, connector portions 550 may be fit over protuberances 537. Connector portions 550 may have a shape corresponding to the shape of protuberances 537. Further, connector portions 550 may be press fit to protuberances 537, according to an exemplary embodiment. According to an exemplary embodiment, protuberances 537 may connect to clevis 506 to attach connector assembly 530 and clevis 506.

Figure 22:
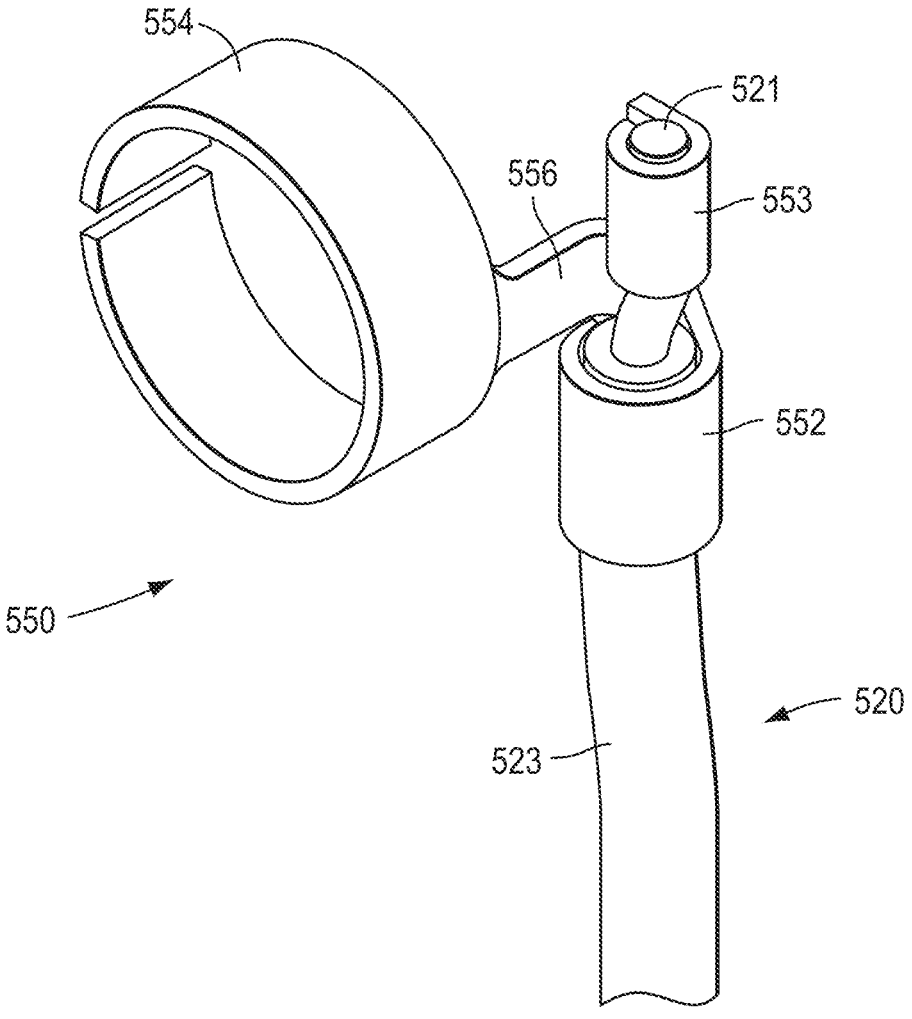
FIG. 22 is a perspective view of an exemplary embodiment of a connection portion of a connector assembly.

Connector portions 550 may include one or more structures to attach a conduit. Turning to FIG. 22, which depicts an exemplary embodiment of conduit 520 attached to connector portion 550, connector portion 550 may include a first attachment 552 to connect connector portion 550 to conduit 520. Connector 550 may further include a second attachment 553, as shown in the exemplary embodiments of FIGS. 21 and 22. For instance, when conduit 520 includes more than one component, such as an outer insulative cover 523 and a conductor 521, as shown in the exemplary embodiment of FIG. 22, first attachment 552 may connect to insulative cover 523 while second attachment 553 connects to an exposed portion of conductor 521. Thus, first attachment 552 may be provided, for example, to assist with maintaining a position of conductor 520 relative to connector portion 550, while second attachment 553 is provided to form an electrically conductive contact between connector portion 550 and conduit 520, particularly conductor 521. Attachments 552, 553 may be attached to conduit 520 via a mechanical connection, such as, for example, crimping attachments 552, 553 to conduit 520, via a bond, such as solder (e.g., soldering attachment 553 to conductor 521), or other joining method known to one of ordinary skill in the art. Conduit 522 may be connected to connector portion 550 in the same way, according to an exemplary embodiment.

Connector portions 550 may further include one or more structures to contact a portion of an end effector. For instance, connector portions 550 may include a contact portion 554 to contact at least one of jaws 502, 504. Contact portion 554 may contact at least one of jaws 502, 504 via sliding contact, according to an exemplary embodiment. For instance, as shown in the exemplary embodiment of FIG. 18, jaw 504 may include an aperture 505 so that jaw 504 may be fit over contact portion 554. Further, aperture 505 may be structured to have a shape and size corresponding to contact portion 554 so that the portion of jaw 504 forming aperture 505 is in contact with contact portion 554. For instance, contact portions 554 may have a split ring shape, as shown in the exemplary embodiments of FIGS. 19, 21, and 22. Thus, when jaw 504 moves, such as by pivoting in direction 540 relative to pin 508, jaw 504 remains in contact with contact portion 554. Jaw 502 may be configured according to the exemplary embodiments of jaw 504 to also form a sliding contact with a contact portion 554 of a connector assembly 530. By configuring contact portions 554 of connectors 530 to contact jaws 502, 504 via sliding contact, a connection, such as an electrical connection, may be provided between conduits 520, 522 and jaws 502, 504 that is advantageously durable while permitting movement of jaws 502, 504 and providing energy to jaws 502, 504 from conduits 502, 504.

According to an exemplary embodiment, connectors 530 may be configured so that jaws 502, 504 move independently of contact portions 554. For instance, when jaws 502, 504 move, such as when jaws 502, 504 are actuated to pivot in direction 540 about pin 508, as shown in the exemplary embodiment of FIGS. 18 and 19, contact portion 554 remains substantially stationary as jaw 504 slides over contact portion 554. As a result, conduits 520, 522 connected to connectors 530 may also remain substantially stationary as jaws 502, 504, which may advantageously minimize or reduce wear or deformation of conduits 520, 522 and connections between conduits 520, 522 and connectors 530. Further, conduits 520, 522 are not directly connected to jaws 502, 504 because connectors 530 form connections between conduits 520, 522 and jaws 502, 504.

According to an exemplary embodiment, a contact portion 554 may be connected to the one or more attachment(s) 552, 553 of connector portions 550 by a bridge 556, as shown in the exemplary embodiment of FIG. 22. According to an exemplary embodiment, connector portions 550 may have a single piece construction. For instance, the one or more attachment(s) 552, 553, contact portion 554, and bridge 556 may be formed from a single piece, although the exemplary embodiments of connector portions 550 described herein are not limited to a single piece construction.

According to an exemplary embodiment, connection portions 550 may be made of a conductive material, such as an electrically conductive material, so that energy provided by conduits 520, 522 may be provided to jaws 502, 504 via connector portions 550. For example, connection portions 550 may be made of a metal, such as, for example, a stainless steel.

By providing a surgical instrument with a push/pull drive element according to the exemplary embodiments described herein, a connection may be advantageously provided between the push/pull drive element and a component of the surgical instrument that has enhanced durability while permitting push/pull drive element to move and actuate an end effector of the surgical instrument. Further, by providing a connector that permits sliding contact and/or independent movement between an end effector and the connector, a connection may be advantageously provided between one or more conduits and the end effector that is durable, while permitting movement of the end effector and providing energy to the end effector from the one or more conduit(s).

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are nonlimiting, and modifications to structure, dimensions, materials, and methodologies may be made without departing from the scope of the present disclosure and claims, including equivalents.

Other embodiments in accordance with the present disclosure will be apparent to those skilled in the art from consideration of the specification and practice of the present disclosure and claims. It is intended that the specification and examples be considered as exemplary only, with the claims being entitled to their full scope and breadth, including equivalents.

What is claimed is:

1. An electrical connector assembly for delivering electrical energy to energize an end effector of a medical instrument, the electrical connector assembly comprising:

an electrical transmission conduit configured to extend along a shaft of the medical instrument, the electrical transmission conduit configured to transmit electrosurgical energy; and a connector assembly coupled to the electrical transmission conduit, the connector assembly comprising:

an electrically insulating member; and an electrically conductive contact portion electrically coupled to the electrical transmission conduit, the electrically conductive contact portion coupled with the electrically insulative member, wherein the electrically conductive contact portion is configured to pivotably couple to the end effector of the medical instrument and define a pivot surface about which the end effector is rotatable, and wherein the electrically insulating member is configured to electrically insulate the end effector from other portions of the medical instrument in a coupled state of the connector assembly to the end effector.

2. The electrical connector assembly of claim 1, wherein the electrically insulating member comprises a U-shaped body portion comprising a first leg and a second leg, and a cavity defined between the first leg and the second leg, wherein the cavity is configured to receive and permit sliding translation of a translating drive element.

3. The electrical connector assembly of claim 1, wherein the electrical transmission conduit is a first electrical transmission conduit and the electrical connector assembly further comprises a second electrical transmission conduit configured to extend along the shaft of the medical instrument and configured to transmit electrical energy, and wherein the electrically conductive contact portion is a first electrically conductive contact portion and the electrical connector assembly further comprises a second electrically conductive contact electrically coupled with the second electrical transmission conduit and coupled with the electrically insulating member.

4. The electrical connector assembly of claim 3, wherein the electrically insulating member further comprises a U-shaped body portion comprising a first leg and a second leg, wherein the first leg comprises a cavity configured to receive the first electrical transmission conduit, and wherein the second leg comprises a cavity configured to receive the second electrical transmission conduit.

5. The electrical connector assembly of claim 4, wherein the U-shaped body portion defines a cavity between the first and second legs, the cavity configured to receive and permit sliding translation of a translating drive element.

6. The electrical connector assembly of claim 2, wherein the U-shaped body portion comprises a protuberance and the electrically conductive contact portion is coupled to the protuberance.

7. The electrical connector assembly of claim 6, wherein the electrically conductive contact portion is a split ring member configured to receive the protuberance.

8. The electrical connector assembly of claim 6, wherein the connector assembly further comprises an attachment member, the attachment member coupled to the electrically conductive contact portion and to the electrical transmission conduit.

9. A method of assembling a medical instrument, the method comprising:

coupling an end effector to a shaft of the medical instrument via a clevis;

electrically coupling an electrical transmission conduit to an electrical connector assembly;

pivotably coupling the electrical connector assembly to the end effector at an electrically conductive contact portion of the electrical connector assembly;

engaging an electrically insulating member of the electrical connector assembly with the clevis; and engaging a translating drive element to the end effector by coupling a head of the drive element oriented along a direction perpendicular to a direction of translation of the drive element with the end effector, the head configured to move relative to a portion of the end effector and in a cavity defined by the electrical connector assembly to actuate movement of the end effector.

10. The method of claim 9, wherein the electrical transmission conduit is a first electrical transmission conduit, and the method further comprises electrically coupling a second electrical transmission conduit to an electrical connector assembly.

11. The method of claim 10, wherein the electrical connector assembly comprises a U-shaped body portion with a first leg defining a first cavity and a second leg defining a second cavity, wherein electrically coupling the first electrical transmission conduit comprises inserting the first electrical transmission conduit in the first cavity of the first leg, and wherein electrically coupling the second electrical transmission conduit comprises inserting the second electrical transmission conduit into the second cavity of the second leg.

12. The method of claim 11, wherein the U-shaped body portion defines the cavity between the first and second legs, and the translating drive element is received in the cavity.

13. A method of delivering electrical energy to energize an end effector coupled via a clevis to a shaft of a medical instrument, the method comprising:

transmitting electrical energy to energize the end effector via an electrical transmission conduit extending along the shaft from a proximal portion to a distal portion;

conducting the electrical energy from the electrical transmission conduit via an electrically conductive contact portion of a connector assembly coupled to the electrical transmission conduit and pivotably coupled to the end effector; and electrically insulating the end effector from the clevis via the connector assembly.

14. The method of claim 13, further comprising actuating movement of the end effector via a translating drive element.

15. The method of claim 14, wherein the end effector comprises jaw members and actuating the jaw members comprises opening or closing the jaw members relative to each other.

16. The method of claim 15, wherein actuating the jaw members comprises pivoting the jaw members relative to the connector assembly.

17. The method of claim 14, wherein actuating the movement of the end effector comprises translating the translating drive element so as to translate a head of the drive element oriented along a direction perpendicular to a direction of translation of the drive element, the head moving relative to a portion of the end effector and in a cavity defined by the connector assembly.

18. The method of claim 13, wherein the electrically conductive contact portion defines a pivot surface about which the end effector is pivotable.

* * * * *